US007365099B2

(12) United States Patent
Pariza et al.

(10) Patent No.: US 7,365,099 B2
(45) Date of Patent: Apr. 29, 2008

(54) ANIMAL BODY FAT CONTROL

(75) Inventors: Michael W. Pariza, Madison, WI (US); Yeonhwa Park, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/871,125

(22) Filed: May 31, 2001

(65) Prior Publication Data

US 2002/0197301 A1   Dec. 26, 2002

(51) Int. Cl.
*A61K 31/00*   (2006.01)
*A61K 31/045*   (2006.01)
(52) U.S. Cl. ........................ 514/734; 514/736; 514/739
(58) Field of Classification Search ................ 514/739, 514/736, 734, 418
See application file for complete search history.

(56) References Cited

U.S. PATENT DOCUMENTS

| 5,554,646 A | 9/1996 | Cook et al. |
| 5,814,663 A | 9/1998 | Cook et al. |
| 5,827,898 A | 10/1998 | Khandwala et al. |
| 6,077,868 A | 6/2000 | Cook et al. |

OTHER PUBLICATIONS

Voet and Voet, Biochemistry, published by John Wiley & Sons, 1990, p. 271-274.*
Verrando et al., Biochemica et Biophysica Acta, 1981; 663: 255-265.*
Miller et al., Biochemical and Biophysical Research Communications, 1994; 198: 1107-1112.*
Steinhart, Journal of Chemical Education, 1996;73(12):A302.*
Parke et al., Biochemical Society Transactions (1973), 1(2), 511-14.*
Park, et al., *Effect of Conjugated Linoleic Acid on Body Composition in Mice*, 32, No. 8 Lipids 853-858 (1997).
Cook, et al., 2 FASEB J. A836 (1998).
Park, et al., *Evidence That the trans-10,cis-12 Isomer of Conjugated Linoleic Acid Induces Body Composition Changes in Mice*, 34,3 Lipids 235-241 (1999).
Liu and Belury, *Conjugated linoleic acid reduces arachidonic acid content and $PGE_2$ synthesis in murine keratinocytes*, 127 Cancer Letters 15-22 (1998).
Choi, et al. *The trans-10,cis-12 Isomer of Conjugated Linoleic Acid Downregulates Stearoyl-CoA Desaturase 1 Gene Expression in 3T3-L1 Adipocytes*[1] , Nutrient-Gene Expression 1920-1924 (2000).
Park, et al., *Inhibition of hepatic steroyl-CoA desaturase activity by trans-10,cis-12 conjugated linoleic acid and its derivatives*, 1486 Biochimica et Biophysica Acta 285-292 (2000).
Cook, et al., *Immune Modulation by Altered Nutrient Metabolism Nutritional Control of Immune-Induced Growth Depression*, 72 Poultry Science Table 1, 1304 (1993).
Cook, et al., Abstract *Regulation of inducible prostanoids and leukotrienes by conjugated linoleic acid (CLA)*, American Chemical Society National Meeting, Washington DC (2000).
Gowri, M.S., et al, "Masoprocol decreases rat lipolytic activity by decreasing the phosphorylation of HSL." Am J Physiol Endocrinol Metab, 279, p. E593-E600, 2000.
Kyoden Yasumoto, Aijior Yamanoto, Hisateru Mitsuda, "Effect of Phenolic Antioxidants on Lipoxygenase Reaction," Jan. 19, 1970, 8 pages, vol. 34, Agr. Biol. Chem. Kyoto.

* cited by examiner

*Primary Examiner*—San-Ming Hui
(74) *Attorney, Agent, or Firm*—Quarles & Brady LLP

(57) ABSTRACT

A method for controlling body fat in a human or nonhuman animal includes the step of reducing lipoxygenase activity in an animal. Lipoxygenase activity can be reduced by reducing the enzyme activity or by lowering the enzyme level. Reduced lipoxygenase activity correlates with reduced cell-associated LPL activity and with reduced cellular triacylglyceride level.

6 Claims, 5 Drawing Sheets

ANIMAL BODY FAT CONTROL

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Control of body fat in human and non-human animals is an ongoing concern and many approaches are sought for achieving body fat control. One goal in the meat industry is to increase the percentage of lean meat in animals. It is therefor desirable to reduce animal body fat because, in general a lower body fat level leads to a higher muscle-to-fat ratio. It is also desirable in many situations in the medical and veterinary arts to reduce fat accumulation in adipocytes. For example, in obese human and non-human animals, adipocytes that accumulate excess lipids can become insulin resistant, a characteristic having many adverse effects including the development of diabetes.

Conjugated linoleic acid (CLA), a set of geometric isomers of a conjugated 18 carbon molecule, controls body composition in animals, in that it reduces body fat gain while increasing lean body mass gain. Park, Y., *Regulation of energy metabolism and the catabolic effects of immune stimulation by conjugated linoleic acid*, Ph.D. Thesis, University of Wisconsin-Madison(1996); Park, Y. et al., *Lipids* 32: 853–858(1997); Cook, M. E. et al., *FASEB J.* 12: A826(1998). The exact mechanism by which CLA affects body composition is unknown. Animals share a conserved mechanism for accumulating fat in fat cells ("adipocytes"), namely, the heparin-releasable lipoprotein lipase (LPL) enzyme located outside of the adipocytes breaks down triglycerides to fatty acids. The fatty acids are absorbed into the adipocytes and are converted into triacylglycerides ("fat") for storage. CLA reduces body fat accumulation, in part, by inhibiting the LPL and stearoyl-CoA desaturase (SCD), thereby preventing adipocytes from storing fat. CLA also increases β-oxidation in skeletal muscle, and increases skeletal muscle mass. Park, Y. et al., *Lipids* 32: 853–858 (1997). In addition to having these effects in mice, CLA also reduces fat accumulation in other animals such as human beings, pigs and dogs. Park, Y. et al., *Lipids* 34: 235–241 (1999); Dugan, M. E. R. and J. L. Aalhus, *Advances in Conjugated Linoleic Acid Research, Vol.* 1: 354–368(1999); Ostrowska, E. et al., *J. Nutr.* 129: 2037–2042(1999); Schoenherr, W. and D. Jewell, *FASEB J* 13: A262(1999); Atkinson, R. L., *Advances in Conjugated Linoleic Acid Research, Vol.* 1: 348–353(1999); Blankson, H. et al., *J. Nutrit.* 130: 2943–2948(2000).

CLA also has many other biological activities including growth promotion activity, Chin, S. F. et al., *J. Nutr.* 124: 2344–2349(1994), anti-atherosclerosis activity, Lee, K. N. et al., *Atherosclerosis* 108: 19–25(1994); Nicolosi, R. J. et al., *Artery* 22: 266–277(1997), and anti-cancer activity, Ha, Y. L. et al., *Cancer Res.* 50: 1097–1101(1990); Ip, C. et al., *Cancer Res.* 51: 6118–6124(1991); Liew, C. et al., *Carcinogenesis* 16: 3037–3043(1995).

At a cellular level, CLA decreases the level of arachidonic acid (AA) in certain animal tissues. AA is oxidized by cyclooxygenase or by lipoxygenases to produce eicosanoid metabolites such as prostaglandin $E_2$ ($PGE_2$) and leukotrienes (LTs). The AA metabolism pathway and the activity of lipoxygenase in the pathway are conserved in animals. Eicosanoids have been implicated in the pathogenesis of a variety of human diseases, including cancer. Ara, G. and B. A. Teicher, *Essential Fatty Acids* 54: 3–16(1996); Fosslien, E., *Annals Clin. Lab. Sci.* 28: 67–81(1998); Steele et al., *Cancer Epi. Biomarker Prev.* 8: 467–483(1999); Myers, C. E. and J. Ghosh, *Eur. Uro.* 35: 395–398(1999). It has been suggested that CLA's anticancer mechanism may involve eicosanoid metabolism. Cook, M. E. et al., *Poultry Sci.* 72: 1301–1305(1993); Liu, K. -L. and M. A. Belury, *Cancer Lett* 127: 15–22(1998); Whigham, L. et al., *FASEB J.* 14: A728 (2000).

Lipoxygenase inhibitor nordihydroguaiaretic acid (NDGA) was reported to reduce lipolysis, the fat degradation process, in fat tissue. Gowri, M. S. et al., *Am. J. Physiol. Endocrinol. Metab.* 279(3): E593-E600 (2000).

BRIEF SUMMARY OF THE INVENTION

The present invention is summarized in that a method for controlling body fat level in a human or nonhuman animal includes the step of administering an agent that reduces lipoxygenase activity in an amount sufficient to control body fat in the animal.

In a related embodiment, the agent that reduces lipoxygenase activity is an agent that directly or indirectly affects the lipoxygenase enzyme's ability to function. In a second related embodiment, the agent that directly or indirectly reduces lipoxygenase activity is an agent that reduces the level of lipoxygenase enzyme in cells in the animal that contain the enzyme. Both classes of such agents are referred to herein as lipoxygenase inhibitors. In a third related embodiment, a combination of agents can be administered to the animals, the agents being added in amounts sufficient in combination to control body fat as detailed herein.

In yet another embodiment, the method includes the steps of administering both an agent that reduces lipoxygenase activity and an agent that comprises trans-10, cis-12 conjugated linoleic acid in amounts effective to elicit a synergistic body fat controlling effect in an animal when the amounts of both agents are separately effective to control body fat.

The method as summarized meets the stated objects of the invention. Other objects, features and advantages of the invention will become apparent upon consideration of the following detailed description.

DETAILED DESCRIPTION OF THE INVENTION

Figure 1:
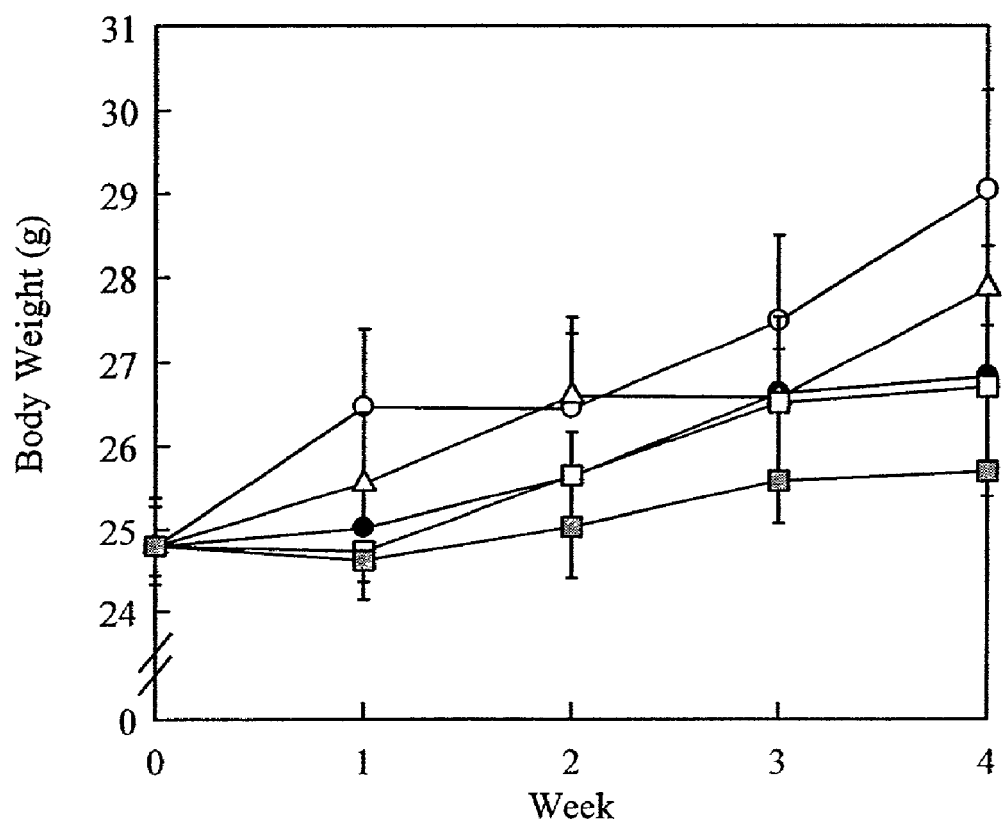
FIG. 1 shows effects of aspirin on body weights in mice.

The present invention relates to controlling body fat in a human or nonhuman animal by reducing lipoxygenase activity in the animal. In this patent application, body fat is "controlled" if the percentage of total body fat is lower after treatment in the method than it would have been without treatment. Preferably treatment is for at least four weeks, although an effect may be observed sooner. Where one can observe both test and control animals (i.e., some non-human animals), one can readily determine whether the total body fat percentage of treated animals is lower than in untreated animals, even where the percentage in untreated animals trends higher or lower. Where no such control population is available, i.e., for humans and other non-human animals, one can instead note the percentage of total body fat just before treatment and compare it to the percentage after treatment, which will be no higher. In an animal in which body fat percentage is increasing, treatment according to the method can slow the rate of increase, can prevent an increase or can cause a decline in the total body fat percentage. In an animal in which body fat percentage is constant, treatment according to the method can cause a decline in the total body fat percentage. In an animal in which body fat percentage is declining, treatment according to the method can enhance the rate of decline.

The method for controlling body fat percentage by reducing lipoxygenase activity is effective in any animal having an arachidonic acid metabolic pathway that involves the lipoxygenase enzyme. These animals include but are not limited to mammals, avian animals and fish. Mammals include but are not limited to humans, primates, bovines, canines, porcines, ovines, caprines, felines and rodents. Avian animals include but are not limited to chickens, ducks, turkeys and quails.

A lipoxygenase inhibitor can be administered into the animal by any convenient delivery means including but not limited to oral administration, intravenous or intramuscular injection, transdermal absorption, parenteral or enteral administration, or delivery directly into fat tissue. Oral administration is generally a preferred delivery means. The inhibitor can be added into an animal's diet or can be administered in tablet form. A suitable daily dose can range from about 0.01% to about 5% by weight in diet, more preferably in the range of from about 0.05% to about 1% by weight in diet, and still more preferably in the range of from about 0.1% to about 0.5% by weight in diet. The term "about" used before a specific dose encompasses variations from the stated dose that achieve a comparable effect in the animal. One of ordinary skill in the art knows how to determine effective dose ranges when a method of administering an inhibitor other than feeding inhibitor-containing diet is used. For example, blood concentration of an inhibitor can be used as a standard to determine a dose equivalent of 0.1% inhibitor by weight in diet in another method of administering the inhibitor.

Any lipoxygenase inhibitor with tolerable side effects can be used to reduce body fat in an animal. The delivered lipoxygenase inhibitor need not directly interact with the lipoxygenase enzyme. Rather, the delivered inhibitor can be metabolized into a product having lipoxygenase-inhibiting activity. Alternatively, the delivered inhibitor can catalyze a reaction, or cascade of reactions, having at least one product having lipoxygenase-inhibiting activity that inhibits lipoxygenase to an extent sufficient to control total body fat percentage in the treated animal. Suitable lipoxygenase inhibitors include but are not limited to NDGA, 2-[12-hydroxydodeca-5,10-diynyl]-3,5,6-trimethyl-p-benzoquinone (AA861), 5,8,11,14-eicosatetraynoic acid (ETYA), indomethacin, salicylhydroxamic acid (SHA), Baicalein, 3,4-dihydroxycinnamic acid (Caffeic acid), cinnamyl-3,4-dihydroxy-a-cyanocinnamate (CDC), Gossypol, 5,6-dehydro arachidonic acid, Baeomycesic acid, Baicalein monohydrate, 3,4-dihydroxyphenyl ethanol, 4,5-dehydro docosahexaenoic acid, eicosatriynoic acid, 5-HETE lactone, 5(S)-HpETE, 12(S)-HpETE, 15(S)-HpETE, 15(S)-HETrE, 9,12-octadecadiynoic acid, a-pentyl-3-(2-quinolinylmethoxy)-benzenemethanol (REV 5901), BHA, BHT, 3-amino-1-/m-(trifluoromethyl)phenyl/-2-pyrazoline (BW755C), and 6,9-diepoxy-6,9-phenylimino-delta 6,8-prostaglandin I 1 (U-60275). Some of the lipoxygenase inhibitors mentioned above, such as indomethacin, cross-inhibit cyclooxygenase. It is the lipoxygenase inhibiting activity of these inhibitors that provides the body fat control effect as the effect of body fat control was not observed with cyclooxygenase-specific inhibitor aspirin.

Baicalein, 3,4-dihydroxycinnamic acid (Caffeic acid), cinnamyl-3,4-dihydroxy-a-cyanocinnamate (CDC) and Gossypol can be obtained from Oxford Biomedical Research; 5,6-dehydro arachidonic acid, Baeomycesic acid, Baicalein monohydrate, 3,4-dihydroxyphenyl ethanol, 4,5-dehydro docosahexaenoic acid, eicosatriynoic acid, 5-HETE lactone, 5(S)-HpETE, 12(S)-HpETE, 15(S)-HpETE, 15(S)-HETrE, 9,12-octadecadiynoic acid and a-pentyl-3-(2-quinolinylmethoxy)-benzenemethanol (REV 5901) can be obtained from Cayman Chemical; and BHA, BHT, 3-amino-1-/m-(trifluoromethyl)phenyl/-2-pyrazoline (BW755C) and 6,9-diepoxy-6,9-phenylimino-delta 6,8-prostaglandin I 1 (U-60275) can be obtained from Prostaglanins and Related Substances.

Another suitable inhibitor of lipoxygenase activity is an antibody that can block the function of a lipoxygenase protein when administered into an animal. When injected intravenously, the dose of an antibody can range from about 0.01 mg to about 100 mg, from about 0.1 mg to about 10 mg, or from about 0.2 mg to about 1.0 mg. The half life of an antibody in an animal can be as long as 2–3 weeks. One of ordinary skill in the art knows how to make a monoclonal or a polyclonal antibody to an enzyme where the nucleic acid and amino acid sequences are published and available to one of ordinary skill in the art. Suitable anti-lipoxygenase antibodies are also commercially available from Research Diagnostics, Inc., Flanders, N.J.

One can also reduce lipoxygenase enzyme activity by lowering the enzyme level by, e.g., increasing the rate at which the enzyme is degraded or reducing the rate at which the enzyme is synthesized, either at the transcriptional level or translational level. One way to block translation of lipoxygenase synthesis is to expose the lipoxygenase-producing cells to an antisense oligonucleotide (DNA or RNA) having a sequence complementary to at least part of the mRNA sequence that encodes the protein. The cDNA sequences of lipoxygenase from many animals are published and available to one of ordinary skill in the art. One of ordinary skill in the art knows how to make and use an antisense oligonucleotide to block the synthesis of the enzyme. For example, one can prepare 20–25 mer antisense oligonucleotides directed against 5' end of lipoxygenase with phosphorothiate derivatives on the last three base pairs on the 3' and 5' end to enhance half life and stability of the oligonucleotide. A useful strategy is to design several oligonucleotides with sequence that extends 2–5 base pairs beyond the 5' start site of transcription.

Any appropriate routes known to one of ordinary skill in the art to administer an antisense oligonucleotide into an animal can be used for the present invention. A carrier for an antisense oligonucleotide can be used to facilitate the process. An example of suitable carriers is Cationic liposome. For example, an oligonucleotide can be mixed with cationic liposomes prepared by mixing 1-alpha dioleylphatidylcelthanolamine with dimethldioctadecylammonium bromide in a ration of 5:2 in 1 ml of chloroform. The solvent will be evaporated and the lipids resuspended by sonication in 10 ml of saline.

The dose of an antisense oligonucleotide used in the present invention can be from about 0.1 μg/kg body weight to about 100 μg/kg body weight, about 1 μg/kg body weight to about 10 μg/kg body weight, or about 3 μg/kg body weight to about 5 μg/kg body weight. Doses outside the above range but block synthesis of a target enzyme can also be used in the present invention.

In another embodiment of the invention, a method for controlling the total body fat percentage of an animal includes the step of administering in the manner described above at least one of the aforementioned agents in combination with a second agent that comprises trans-10, cis-12 conjugated linoleic acid, which combination is shown herein to act synergistically in the control of body fat. The two agents need not be mixed with one another before being administered. CLA can be administered at a dosage ranging from about 0.01% to about 5% by weight in diet, from about 0.05% to about 1% by weight in diet, or from about 0.1% to about 0.5% by weight in diet.

The effectiveness of the aforementioned methods of the invention can be assessed by measuring a reduction in cell-associated, extracellular lipoprotein lipase (LPL) enzyme activity or by measuring a reduction in triacylglycerides in fat cells. Cell-associated LPL is not inside but outside of the cell, either in contact with or in close proximity to the cellular membrane. LPL breaks down triglycerides from the blood into fatty acids that can then enter fat cells and be converted into fat. Without intending to be limited to a theory of the invention, the inventors believe that reduced LPL activity results in a reduced ability of fatty acids to enter fat cells and, hence, a reduced ability to form and store fat in fat cells, thereby contributing at least in part to the body fat-controlling effect of the methods of the invention.

In an example that follows, reduced LPL activity and reduced triacylglyceride levels are observed in vitro after treating cultured 3T3-L1 adipocyte cells with an agent that reduces lipoxygenase activity, whether in combination with or without CLA, using treatment doses that correspond to the doses effective in the disclosed in vivo methods. For example, the in vitro dose of an agent that reduces lipoxygenase activity can range from about 0.1 μM to about 5 mM, from about 10 μM to about 500 μM, or from about 30 μM to about 200 μM. The same dose ranges apply to CLA when CLA is used in combination with an agent that reduces lipoxygenase activity.

The above disclosure generally describes the present invention. The invention will be more fully understood upon consideration of the following examples which are provided herein for purposes of illustration only and are not intended to limit the scope of the invention.

EXAMPLES

Materials

Linoleic acid was purchased from Nu-Chek Corporation, Elysian, Minn.; triolein, [9,10-$^3$H (N)], (specific activity 12 Ci/mmol) from American Radiolabeled Chemicals, St. Louis, Mo.; and [1-$^{14}$C] linoleic acid (specific activity 55 mCi/mmol) from Amersham Life Science, Arlington Heights, Ill. CLA was prepared by alkali isomerization from pure linoleic acid as described (Chin et al. 1992) The CLA used in cell culture experiments was 45.7% cis-9, trans-11, 47.6% trans-10, cis-12, 1.71% trans, trans, 2.77% cis, cis, and 0.27% other isomers. CLA used in the animal experiment contained 38.6% cis-9, trans-11, 38.8% trans-10, cis-12, 9.3% trans, trans, 3.3% cis, cis, and 6.1% other isomers. Acetylsalicylic acid (aspirin), nordihydroguaiaretic acid (NDGA), 2-[12-hydroxydodeca-5,10-diynyl]-3,5,6-trimethyl-p-benzoquinone (AA861), 5,8,11,14-eicosatetraynoic acid (ETYA), and indomethacin was purchased from Sigma Chemical Co., St. Louis, Mo. Salicylhydroxamic acid (SHA) was purchased from Aldrich Chemical, Milwaukee, Wis. Prostaglandin $E_2$ ($PGE_2$) was purchased from Cascade Biochem LTD, England. 3T3-L1 preadipocytes were purchased from American Type Culture Collection, Rockville, Md.

Statistical Analyses

Data were subjected to analysis using the Statistics Analysis System (SAS Users Guide: Statistics, SAS Institute Inc., Cary, N.C.). Data on Tables 1–4, and FIGS. 1 & 2 were analyzed with one-way ANOVA. Two-way ANOVA (treatments and experiments) were performed on data as log value for FIGS. 3–5. If the interaction between treatment and experiment was significant, this interaction was then used as the error term in the Least Square Means analysis.

Results

Experiment 1. Aspirin, an agent that inhibits both cyclooxygenase 1 and 2, had no effect on body composition when fed alone or in combination with CLA.

After a 5 day adaptation period, four-week-old weanling female ICR mice (Harlan Sprague-Dawley) were randomly separated into groups that were fed one of the treatment diets for 4 weeks. Mice were fed either a control diet, or a diet supplemented with aspirin alone (0.03%), 0.5% CLA alone, or CLA with additional aspirin (0.006% ["Asp1"] or 0.03% ["Asp2"]). The control diet was semi-purified TD94060 diet, 99% basal mix from Harlan Teklad, Madison, Wis. that contained (ingredient, g/kg): sucrose, 476; casein, "vitamin-free" test, 210; corn starch, 150; DL-methionine, 3; corn oil 55; cellulose, 50; mineral mix, AIN-76, 35; vitamin mix, AIV-76A, 10; calcium carbonate, 4; choline bitartrate, 2; and ethoxyquin, 0.1. The aspirin doses reflect an average human dose (0.03%) or a recommended dose for preventing cardiovascular disease (0.006%). Supplemental CLA was added to diets at the expense of corn oil. Diet was stored at −20° C. until use. Mice were housed individually in a windowless room with a 12-h light-dark cycle in strict accordance to guidelines established by the Research Animal Resources Center of University of Wisconsin-Madison. Diet and water, available ad libitum, were freshly provided three times per week.

For body composition analyses, animals were sacrificed, gut contents were removed (to obtain empty carcass weight, "ECW"), and the carcasses frozen at −20° C. Frozen carcasses were chopped, and freeze dried to determine water content. Each dried carcass was ground to give a homogeneous sample before further analysis. Total nitrogen was analyzed by the Kjeldahl method. Helrich, K., *Official Methods of Analysis*, 15$^{th}$ ed.: 935–937(1990). Carcass fat content was measured by extraction with diethyl ether overnight using a Soxhlet apparatus. Total ash content was determined by incineration (500–600° C., overnight).

Effects of aspirin on food intake and body composition are shown in Table 1 and Table 2. Results shown are mean±S.E. (n=6). Means with different letters in each column are significantly different at P<0.05. All CLA fed groups ate less food than control or groups with aspirin at all time points.

All CLA-fed groups had decreased fat and increased water and protein, which is consistent with previous reports. Aspirin alone had no effect on body composition and did not change any of CLA's effects at either tested dose.

After a 5 day adaptation period, four-week-old weanling male ICR mice (Harlan Sprague-Dawley) were randomly separated into groups that were fed one of the treatment diets for 4 weeks. Mice were fed either a control diet (as in Experiment 1), or a diet supplemented with CLA (0.1%), NDGA (0.1% or 0.005%), or CLA (0.1%) with NDGA (0.1% or 0.005%). The lower level of NDGA was chosen based on the level used as an antioxidant in the food industry. Supplemental NDGA was added to diets at the expense of sugar. Diet was stored at −20° C. until use. Mice were housed individually in a windowless room with a 12-h light-dark cycle in strict accordance to guidelines established by the Research Animal Resources Center of University of Wisconsin-Madison. Diet and water, available ad libitum, were freshly provided three times per week.

TABLE 1

Effect of aspirin on food intake (g/mouse)

| | Week 1 | Week 2 | Week 3 | Week 4 | Total |
|---|---|---|---|---|---|
| Control | 30.82$^a$ ± 1.21 | 30.57$^a$ ± 1.15 | 29.18$^a$ ± 1.32 | 30.88$^a$ ± 1.09 | 121.5$^a$ ± 4.4 |
| CLA | 24.50$^b$ ± 0.58 | 23.15$^b$ ± 0.79 | 23.77$^b$ ± 0.80 | 24.22$^b$ ± 0.84 | 95.6$^b$ ± 2.5 |
| CLA + Asp1 | 25.15$^b$ ± 0.76 | 24.93$^b$ ± 1.74 | 24.53$^{bc}$ ± 1.54 | 25.63$^b$ ± 1.80 | 100.3$^b$ ± 5.5 |
| CLA + Asp2 | 25.10$^b$ ± 0.57 | 23.68$^b$ ± 0.64 | 24.00$^b$ ± 0.82 | 24.70$^b$ ± 1.03 | 97.5$^b$ ± 2.6 |
| Asp 2 | 30.68$^a$ ± 1.01 | 28.98$^a$ ± 0.90 | 28.30$^{ac}$ ± 1.49 | 31.28$^a$ ± 2.32 | 119.3$^a$ ± 4.4 |

TABLE 2

Effect of aspirin on body composition

| | ECW(g) | % Fat | % Water | % Protein | % Ash |
|---|---|---|---|---|---|
| Control | 27.70$^a$ ± 1.24 | 17.76$^a$ ± 2.51 | 59.86$^{ab}$ ± 1.66 | 16.86$^a$ ± 0.63 | 3.59$^{ab}$ ± 0.18 |
| CLA | 25.19$^b$ ± 0.59 | 12.24$^b$ ± 1.27 | 63.29$^{bc}$ ± 1.08 | 18.01$^{bc}$ ± 0.21 | 3.64$^{ab}$ ± 0.11 |
| CLA + Asp1 | 25.13$^b$ ± 0.93 | 12.34$^b$ ± 1.13 | 62.93$^{bc}$ ± 0.99 | 18.33$^{bc}$ ± 0.17 | 3.73$^{ab}$ ± 0.07 |
| CLA + Asp2 | 24.11$^b$ ± 0.32 | 10.11$^b$ ± 1.62 | 64.29$^c$ ± 1.14 | 18.75$^c$ ± 0.35 | 3.93$^a$ ± 0.05 |
| Asp2 | 26.45$^{ab}$ ± 0.45 | 17.95$^a$ ± 1.02 | 59.19$^a$ ± 0.80 | 17.22$^{ab}$ ± 0.13 | 3.55$^b$ ± 0.05 |

Body weights are shown in FIG. 1 (numbers: mean±S.E. (n=6); control: open circles; CLA: filled circles; CLA plus 0.006% aspirin: open squares; CLA plus 0.03% aspirin: filled squares; and aspirin: open triangles). There was no difference in body weights at weeks 0 through 3. At week 4, all CLA fed animals were slightly smaller, and the body weight of the CLA group given a high dose of aspirin (0.3%) was significantly different from control.

Experiment 2: When fed in an effective amount, NDGA can control body composition and has a synergistic effect when fed in combination with CLA

TABLE 3

Effect of NDGA on food intake (g/mouse)

| | Week 1 | Week 2 | Week 3 | Week 4 | Total |
|---|---|---|---|---|---|
| Control | 34.5 ± 0.8 | 36.4$^a$ ± 1.2 | 35.0$^a$ ± 1.1 | 32.5 ± 0.3 | 138.4 ± 3.1 |
| CLA | 34.5 ± 0.3 | 36.9$^a$ ± 0.6 | 32.7$^b$ ± 0.4 | 32.4 ± 0.7 | 136.6 ± 1.2 |
| NDGA (0.1%) | 35.2 ± 0.7 | 35.5$^{ab}$ ± 0.7 | 33.4$^{ab}$ ± 0.4 | 33.8 ± 1.0 | 137.9 ± 1.9 |
| NDGA(0.005%) | 33.8 ± 0.6 | 34.8$^{ab}$ ± 0.9 | 33.8$^{ab}$ ± 0.3 | 34.0 ± 0.4 | 136.3 ± 1.3 |
| CLA + NDGA(0.1%) | 33.5 ± 0.4 | 33.4$^b$ ± 0.6 | 32.6$^b$ ± 0.7 | 34.3 ± 0.7 | 133.7 ± 1.9 |
| CLA + NDGA(0.005%) | 33.3 ± 0.5 | 35.9$^{ab}$ ± 1.1 | 32.6$^b$ ± 0.9 | 33.9 ± 1.3 | 135.7 ± 3.0 |

TABLE 4

Effect of NDGA on body composition

| | ECW (g) | % Fat | % Water | % Protein | % Ash |
|---|---|---|---|---|---|
| Control | 34.1 ± 1.2 | 18.18$^a$ ± 2.58 | 57.3$^a$ ± 1.9 | 18.80$^a$ ± 0.41 | 3.32 ± 0.09 |
| CLA | 32.0 ± 0.9 | 14.00$^{ab}$ ± 1.79 | 60.2$^{ab}$ ± 1.3 | 19.29$^{ab}$ ± 0.39 | 3.49 ± 0.07 |
| NDGA 0.1% | 31.9 ± 1.3 | 14.30$^{ab}$ ± 1.31 | 60.3$^{ab}$ ± 0.8 | 19.28$^{ab}$ ± 0.30 | 3.43 ± 0.09 |
| NDGA0.005% | 32.2 ± 0.6 | 16.62$^a$ ± 2.34 | 58.3$^a$ ± 1.8 | 18.92$^a$ ± 0.55 | 3.29 ± 0.12 |
| NDGA0.1 + CLA | 31.1 ± 0.5 | 8.96$^b$ ± 1.51 | 64.0$^b$ ± 1.2 | 20.48$^b$ ± 0.34 | 3.66 ± 0.08 |
| NDGA0.005 + CLA | 32.2 ± 1.6 | 17.27$^a$ ± 1.90 | 57.8$^a$ ± 1.3 | 18.49$^a$ ± 0.38 | 3.40 ± 0.22 |

Figure 2:
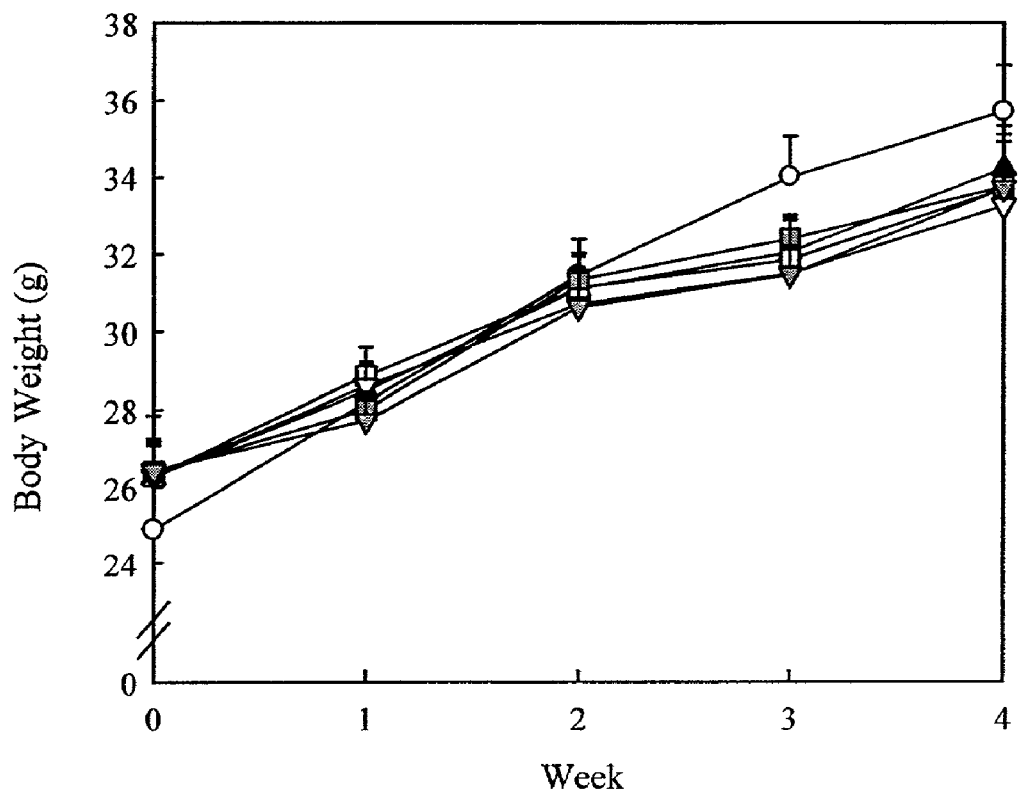
FIG. 2 shows effects of nordihydroguaiaretic acid (NDGA) on body weights in mice.

There was no difference in body weights between groups (FIG. 2: numbers—mean±S.E. (n=5–6); control—open circles; CLA—filled triangles, up; 0.1% NDGA—open squares; 0.005% NDGA—filled squares; CLA plus 0.1% NDGA—open triangles, down; and CLA plus 0.005% NDGA—filled triangles, down). Compared to control, NDGA (0.1%) plus CLA significantly decreased food intake at weeks 2 and 3, while CLA reduced food intake only at week 3 (Table 3). However, there was no significant difference in food intake between groups in the overall period. Body composition (Table 4) indicated that CLA at a 0.1% level reduced fat (p<0.197) and increased water and protein. NDGA at a 0.1% level also reduced fat (p<0.209) and increased water and protein. 0.005% of NDGA had no effect on body composition. When a combination of CLA and NDGA at 0.1% were fed, a synergistic effect on body composition was observed: animals had significantly less fat, and significantly more water and protein compared to control. In contrast, a combination of CLA with NDGA at 0.005% had no effect on body composition. The numbers shown in Table 3 and Table 4 are mean±S.E. (N=5–6). Means with different letters in each column are significantly different at p<0.05.

Experiment 3: LPL activity is inhibited in 3T3-L1 adipocyte cell cultures in the presence of a lipoxygenase inhibitor (NDGA) but not in the presence of a COX-inhibitor (aspirin)

Fat reduction by CLA is partly due to inhibition of lipoprotein lipase (LPL) in adipocytes, as has been previously shown using a 3T3-L1 adipocyte cell culture model. Using the same model, the effects on LPL of aspirin and NDGA, as compared to CLA, were tested. 3T3-L1 preadipocytes were cultured as described. Frost, S. C. and M. D. Lane, *J. Biol. Chem.* 260: 2646–2652(1985). Briefly, 3T3-L1 preadipocytes were grown to confluence at 37° C. in Dulbecco's Modified Eagle's Medium (DMEM) with 10% fetal bovine serum (FBS). At two days post-confluence (designated "day 0") cell differentiation was induced with a mixture of methylisobutylxanthine (0.5 mM), dexamethasone (0.25 μM), and insulin (1 μg/ml) in DMEM containing 10% FBS. On "day 2" this medium was replaced with DMEM medium containing 10% FBS and insulin only. On "day 4" and thereafter the medium was DMEM plus 10% FBS only; this medium was subsequently replaced with fresh medium at 2 day intervals.

First, aspirin was tested along with $PGE_2$, which is the final product of cyclooxygenase. Cells were treated with testing compounds for 4 hours before harvesting at day 6 or 7 post differentiation. The concentration of CLA, aspirin, and $PGE_2$ were $1 \times 10^{-4}$ M, $1 \times 10^{-4}$ M, and $1 \times 10^{-6}$ M respectively. CLA was complexed with albumin as described, Park, Y. et al., *Lipids* 32: 853–858(1997); aspirin and $PGE_2$ were dissolved in ethanol. All dishes (including control) contained the same concentration of albumin ($1 \times 10^{-4}$ M) and ethanol (final concentration of 0.1%).

Heparin-releasable lipoprotein lipase (LPL) activity (EC 3.1.1.34, 10 U heparin/ml media for 1 hr at 37° C.) was measured as described. Nilsson-Ehle, P. and M. C. Schotz, *J. Lipid Res.* 17: 536–541(1976). Recovery of free fatty acid was estimated at 71% by using [1-$^{14}$C] linoleic acid. Protein was determined using Bio-Rad DC Protein assay kit.

Figure 3:
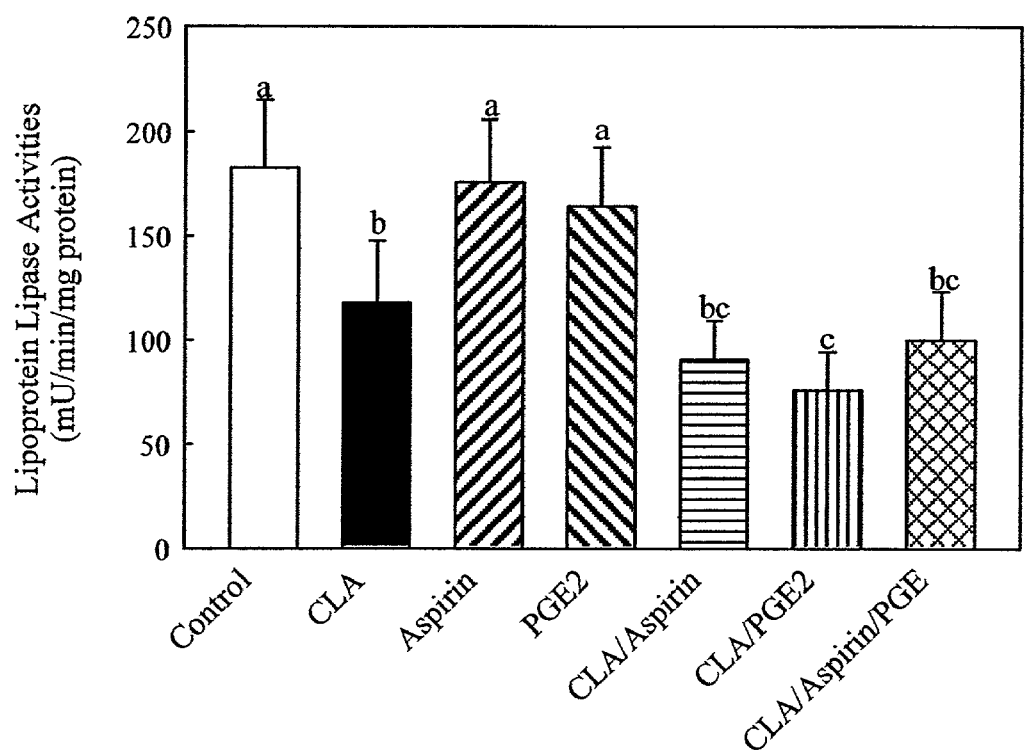
FIG. 3 shows effects of CLA, aspirin, and/or prostaglandin $E_2$ ($PGE_2$) on lipoprotein lipase associated with 3T3-L1 adipocytes.

FIG. 3 shows that CLA (100 μM) significantly decreased LPL activity compared to control, which we previously reported to be due to the trans-10,cis-12 isomer of CLA. $PGE_2$ (1 μM) and aspirin (100 μM) had no effect on LPL. When CLA was added with $PGE_2$, there was a significant reduction of LPL activity compared to control and CLA alone. However, adding aspirin and CLA with or without $PGE_2$, was no different than CLA alone. Numbers in FIG. 3 are mean±S.E. (n=12–13, collected from 3 independent experiments). Means with different letters are significantly different at P<0.05.

Figure 4:
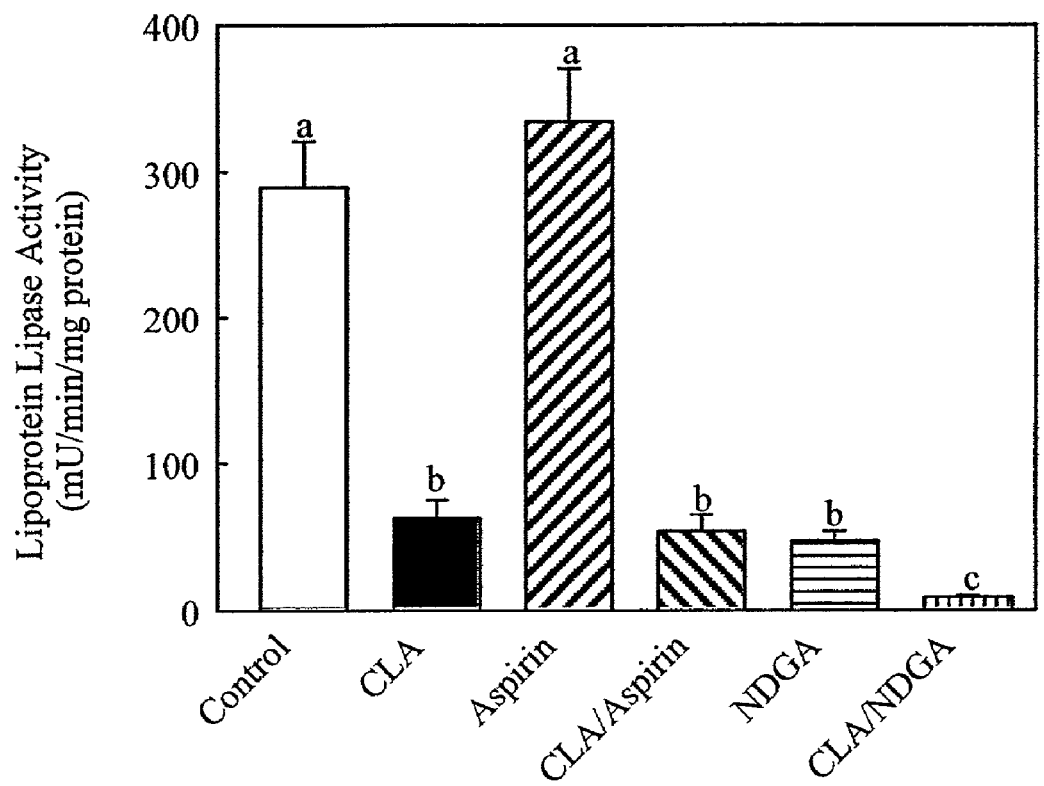
FIG. 4 shows effects of CLA, aspirin, and NDGA on lipoprotein lipase associated with 3T3-L1 adipocytes.
Figure 5:
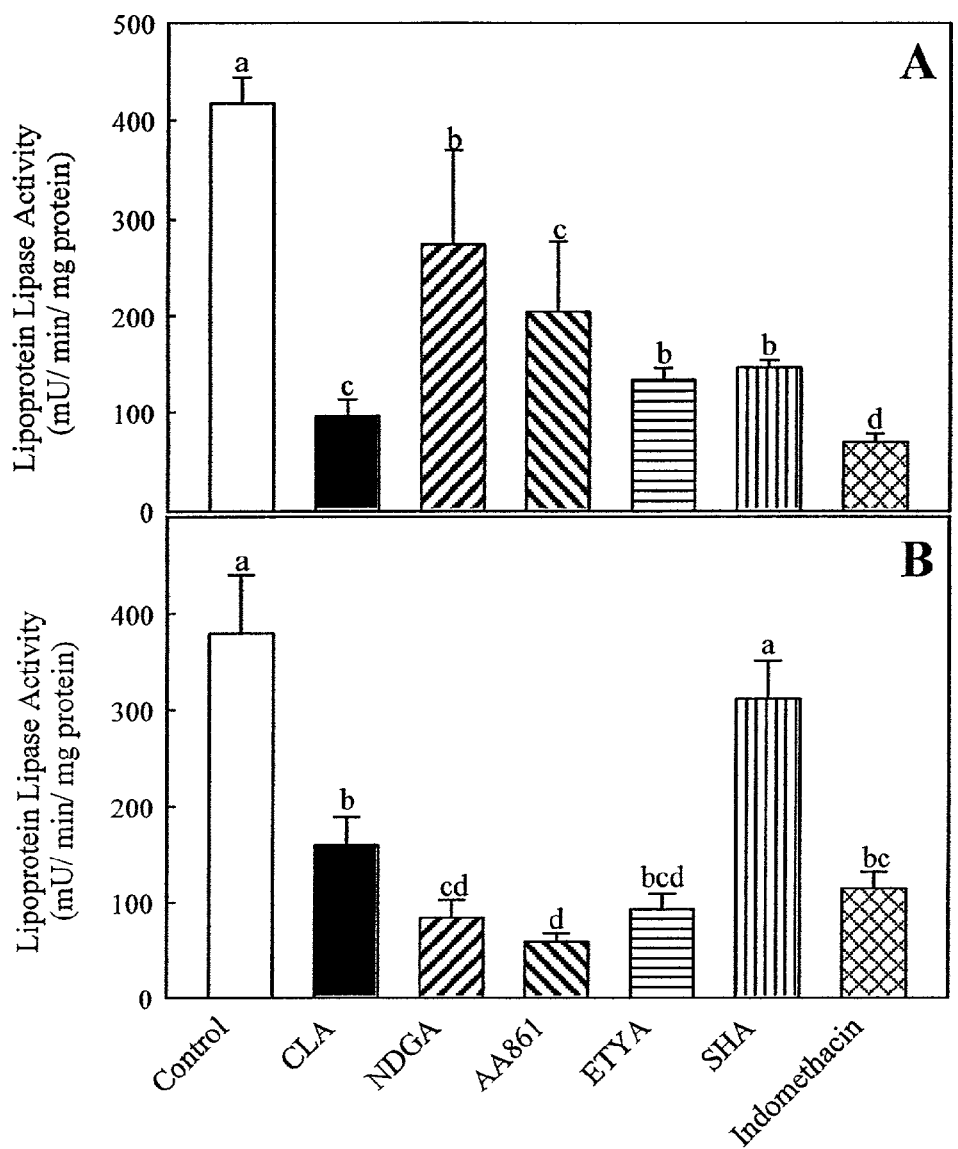
FIG. 5 shows effects of lipoxygenase inhibitors on lipoprotein lipase associated with 3T3-L1 adipocytes.

In a next set of cell culture experiments, shown in FIG. 4, cells were treated with testing compounds for 20–24 hours at day 7 post differentiation. The concentration of CLA, aspirin, and NDGA were $1 \times 10^{-4}$ M, $1 \times 10^{-4}$ M, and $5 \times 10^{-5}$ M respectively. CLA was complexed with albumin, and aspirin and NDGA were dissolved in ethanol. All dishes including control contained the same concentration of albumin ($1 \times 10^{-4}$ M) and ethanol (final concentration of 0.05%). Numbers are mean±S.E. (n=7–8, collected from 2 independent experiments). Means with different letters are significantly different at P<0.05. As was shown in FIG. 3, CLA significantly reduced LPL activity while aspirin had no effect. NDGA (50 μM) significantly reduced LPL activity, which is similar to CLA. When NDGA and CLA were administered in combination, an additional LPL inhibitory effect was observed.

Cells were treated with other known lipoxygenase inhibitors. Cells were treated with testing compounds for 20–24 hours at day 6 or 7 post differentiation. Based on the $ED_{50}$ of these inhibitors, various doses were first tested. In FIG. 5A, the concentration of SHA, CLA, ETYA, indomethacin, NDGA and AA861 were $1 \times 10^{-3}$ M, $1 \times 10^{-4}$ M, $1 \times 10^{-4}$ M, $1 \times 10^{-4}$ M, $1 \times 10^{-5}$ M and $1 \times 10^{-6}$ M, respectively. In FIG. 5B, the cells were treated with the test compounds at $1 \times 10^{-4}$ M. CLA was complexed with albumin and others were dissolved in ethanol. All dishes including control contained the same concentration of albumin ($1 \times 10^{-4}$ M) and ethanol (final concentration of 0.1%). Numbers are mean±S.E. (in FIG. 5A, n=7–8, collected from 2 independent experiments, in FIG. 5B, n=11–12, collected from 3 independent experiments). Means with different letters are significantly different at P<0.05. Indomethacin blocks both cyclooxygenase and lipoxygenase, the two primary enzymes in the arachidonic acid metabolic cascade. All lipoxygenase inhibitors reduced LPL by various degrees. When 100 μM of these were tested, the potency was AA861>NDGA>ETYA> Indomethacin>CLA. SHA had no effect at 100 μM since the $ED_{50}$ of this chemical is $1 \times 10^{-3}$ M. These potency results are consistent with reported $ED_{50}$ for the inhibition of lipoxygenase. Schewe, T. et al., *Prostaglandins and related substances: apractical approach*, 229–242(1987). The amount of cellular triacylglyceride (TG) was reduced by CLA and by various lipoxygenase inhibitors. Only CLA increased the glycerol released from the cell. NDGA and AA861 reduced the glycerol release; the other lipoxygenase inhibitors tested had no effect.

In the above description, the present invention is described in connection with specific examples. It will be understood that the present invention is not limited to these examples, but rather is to be construed to be of spirit and scope defined by the appended claims.

We claim:

1. A method for controlling body fat in an animal having a total body fat percentage, the method comprising the step of:

administering a lipoxygenase inhibitor to the animal in an amount sufficient to control body fat in the animal, wherein the lipoxygenase inhibitor administered is selected from the group consisting of NDGA, AA861, Indomethacin, ETYA, SHA, Baicalein, 3,4-dihydroxycinnamic acid, cinnamyl-3,4-dihydroxy-a-cyanocinnamate, Gossypol, 5,6-dehydro arachidonic acid, Baeomycesic acid, Baicalein monohydrate, 3,4-dihydroxyphenyl ethanol, 4,5-dehydro docosahexaenoic acid, eicosatriynoic acid, 5-HETE lactone, 5(S)-HpETE, 12(S)-HpETE, 15(S)-HpETE, 15(S)-HETrE, 9,12-octadecadiynoic acid, a-pentyl-3-(2-quinolinylmethoxy)-benzenemethanol, 3-amino-1-/m-(trifluoromethyl)phenyl/-2-pyrazoline, and 6,9-diepoxy-6,9-phenyliminodelta 6,8-prostaglandin I 1; and determining total body fat percentage in the animal after administration, where the post-administration percentage is no higher than the percentage before administration.

2. A method for controlling body fat in an animal, the administering step comprising the step of:

feeding NDGA to the animal in an amount sufficient to control body fat in the animal.

3. The method of claim 2, wherein the NDGA is fed in an amount from about 0.01% to about 5% by weight in diet.

4. The method of claim 2, wherein the NDGA is fed in an amount from about 0.05% to about 1% by weight in diet.

5. The method of claim 2, wherein the NDGA is fed in an amount from about 0.1% to about 0.5% by weight in diet.

6. A method for controlling body fat in an animal, the administering step comprising the step of:

administering an anti-lipoxygenase antibody to the animal in an amount sufficient to control body fat in the animal.

* * * * *